United States Patent [19]
Narukawa

[11] Patent Number: 5,137,410
[45] Date of Patent: Aug. 11, 1992

[54] MATERIAL SUPPLY APPARATUS FOR TRANSFERRING POWDERY, GRANULAR AND CONGLOMERATED MATERIALS

[75] Inventor: Akira Narukawa, Yokkaichi, Japan

[73] Assignee: NGK Insulators, Ltd., Japan

[21] Appl. No.: 471,628

[22] Filed: Jan. 29, 1990

Related U.S. Application Data

[62] Division of Ser. No. 235,560, Aug. 24, 1988, Pat. No. 4,919,342.

[30] Foreign Application Priority Data

| Aug. 31, 1987 | [JP] | Japan | 62-215181 |
| Aug. 31, 1987 | [JP] | Japan | 62-215182 |
| Aug. 31, 1987 | [JP] | Japan | 62-215184 |
| Aug. 31, 1987 | [JP] | Japan | 62-215186 |
| Sep. 9, 1987 | [JP] | Japan | 62-224160 |
| Oct. 19, 1987 | [JP] | Japan | 62-261769 |

[51] Int. Cl.$^5$ ............................................. B65G 65/00
[52] U.S. Cl. .................................... 414/415; 414/331; 414/281; 414/273; 414/404; 414/416; 414/421
[58] Field of Search ............... 414/268, 273, 281, 331, 414/413, 415, 419, 421, 403, 404, 416

[56] References Cited

U.S. PATENT DOCUMENTS

| 3,080,078 | 3/1963 | Carew et al. ................. 414/419 X |
| 3,715,040 | 2/1973 | Polus et al. ................. 414/273 X |
| 3,779,410 | 12/1973 | Phillips et al. ................. 414/415 X |
| 3,780,852 | 12/1973 | Weiss et al. ................. 414/331 X |
| 3,879,609 | 4/1975 | VanBaeckmann et al. . |
| 3,922,542 | 11/1975 | Tanguy . |
| 3,966,672 | 6/1976 | Gaylord . |
| 4,493,606 | 1/1985 | Foulke et al. ................. 414/404 X |
| 4,569,623 | 2/1986 | Goldmann ................. 414/415 X |
| 4,582,990 | 4/1986 | Stevens ................. 414/416 X |
| 4,770,593 | 9/1988 | Anderson ................. 414/331 |
| 4,784,333 | 11/1988 | Hikake et al. . |
| 4,874,281 | 10/1989 | Bergerioux et al. ............ 414/273 X |
| 4,982,553 | 1/1991 | Itoh ................. 414/416 X |

FOREIGN PATENT DOCUMENTS

| 114686 | 8/1984 | European Pat. Off. . |
| 1154161 | 9/1963 | Fed. Rep. of Germany ...... 414/415 |
| 1914929 | 11/1969 | Fed. Rep. of Germany . |
| 1811635 | 6/1970 | Fed. Rep. of Germany ...... 414/281 |
| 1461150 | 10/1966 | France ................. 414/281 |
| 2485733 | 6/1980 | France . |
| 52-99885 | 8/1977 | Japan . |
| 0093007 | 5/1985 | Japan ................. 414/331 |
| 0305838 | 9/1968 | Sweden ................. 414/415 |
| 1172840 | 8/1985 | U.S.S.R. ................. 414/331 |

OTHER PUBLICATIONS

Journal of Analytical Chemistry of the USSR, vol. 38, No. 12, part 1, pp. 1640-1645, Dec. 1983.
"Zirconium-containing Synthetic Standard Specimens for X-ray Flourescence Apparatus", Measurement Techniques, vol. 27, No. 1, Jan. 1984, pp. 102-103, B. Y. Dundua et al.

*Primary Examiner*—Frank E. Werner
*Attorney, Agent, or Firm*—Parkhurst, Wendel & Rossi

[57] ABSTRACT

A material supply apparatus for transferring powdery, granular and conglomerated materials, including a base member, a material vessel pooling unit, a plurality of elongate material racks arranged side by side in the material vessel pooling unit, a plurality of material vessels arranged in each of the elongate material racks, a material vessel transferring unit for removing and transferring a selected material vessel from a selected elongate material rack, and control devices for controlling movement of the material vessel pooling unit and for controlling movement of the material vessel transferring unit.

4 Claims, 4 Drawing Sheets

FIG_1
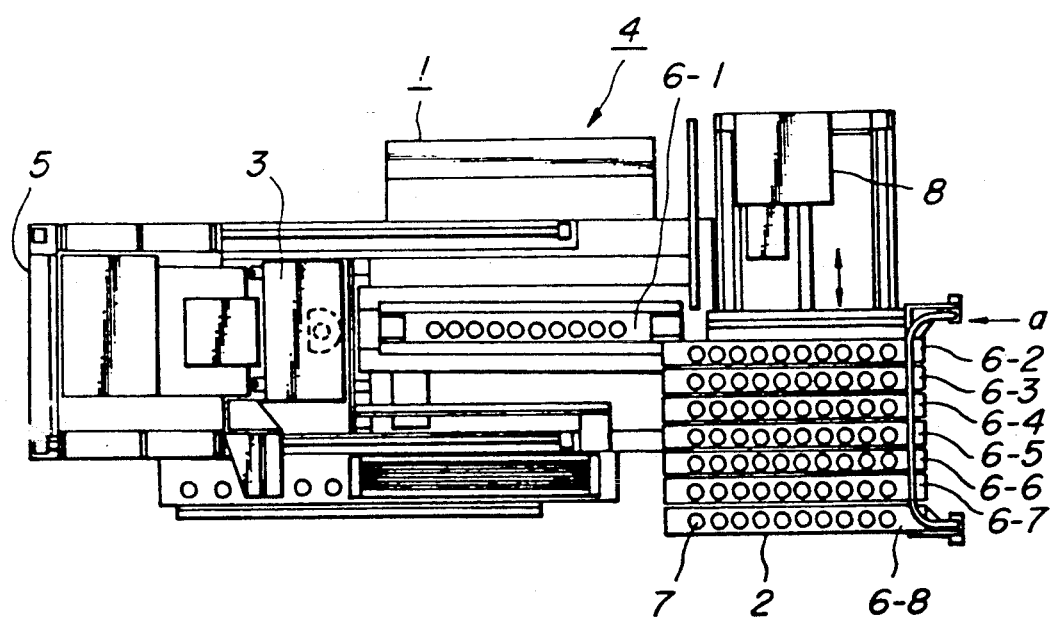

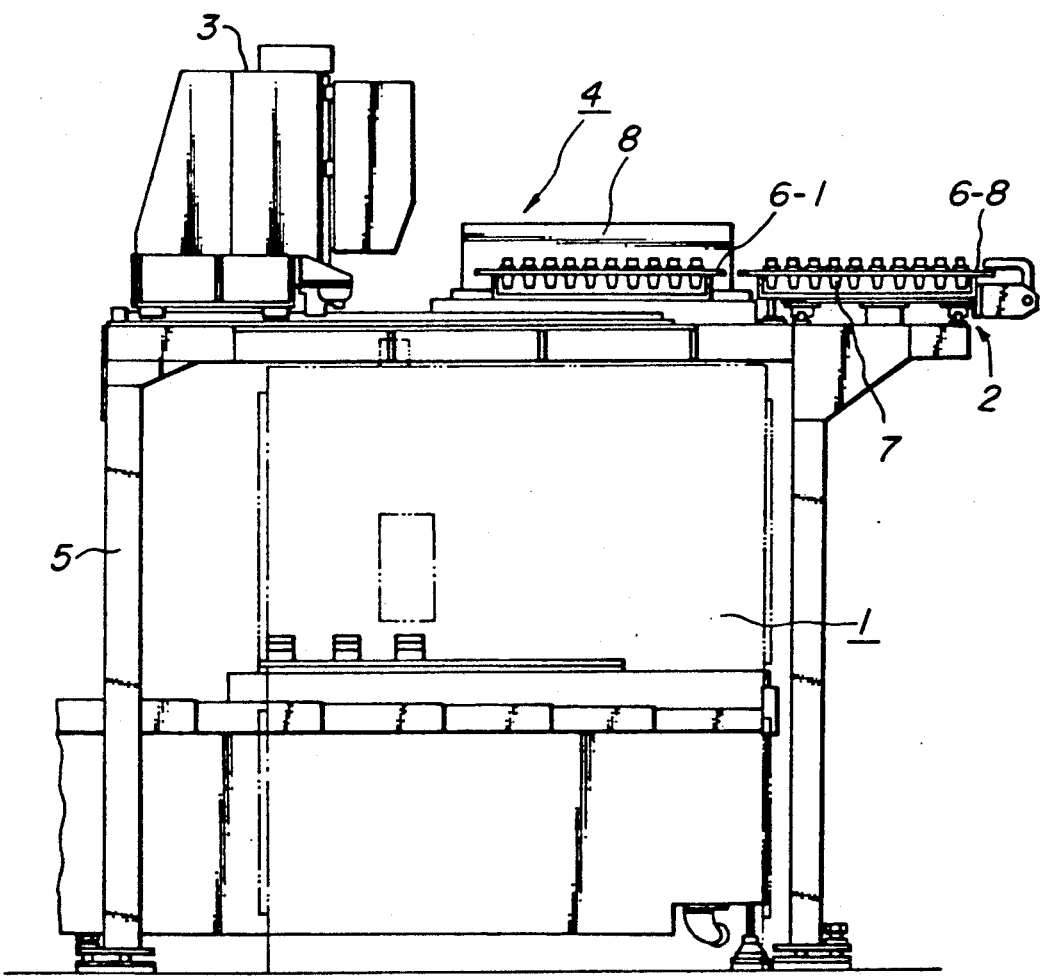
FIG_2

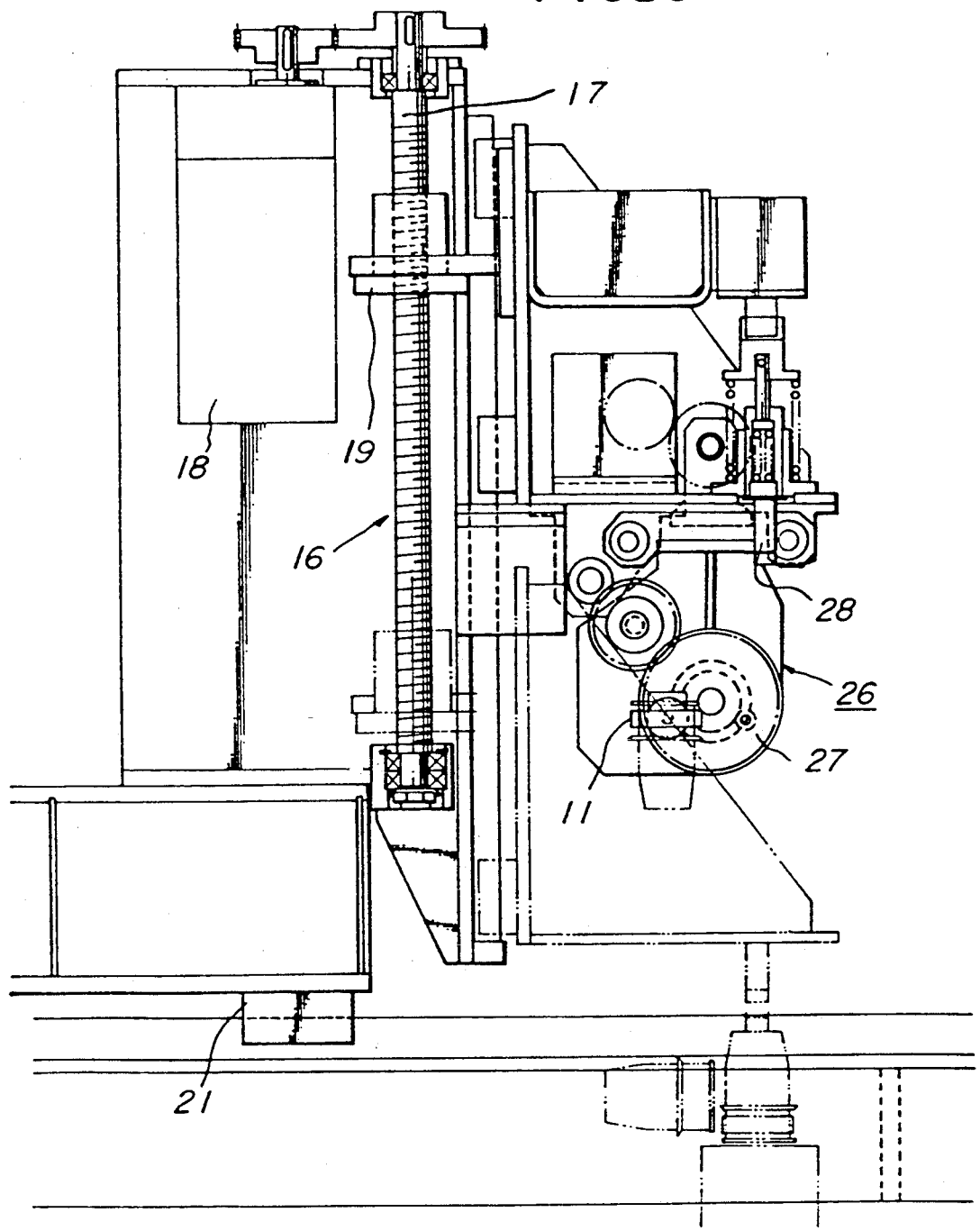

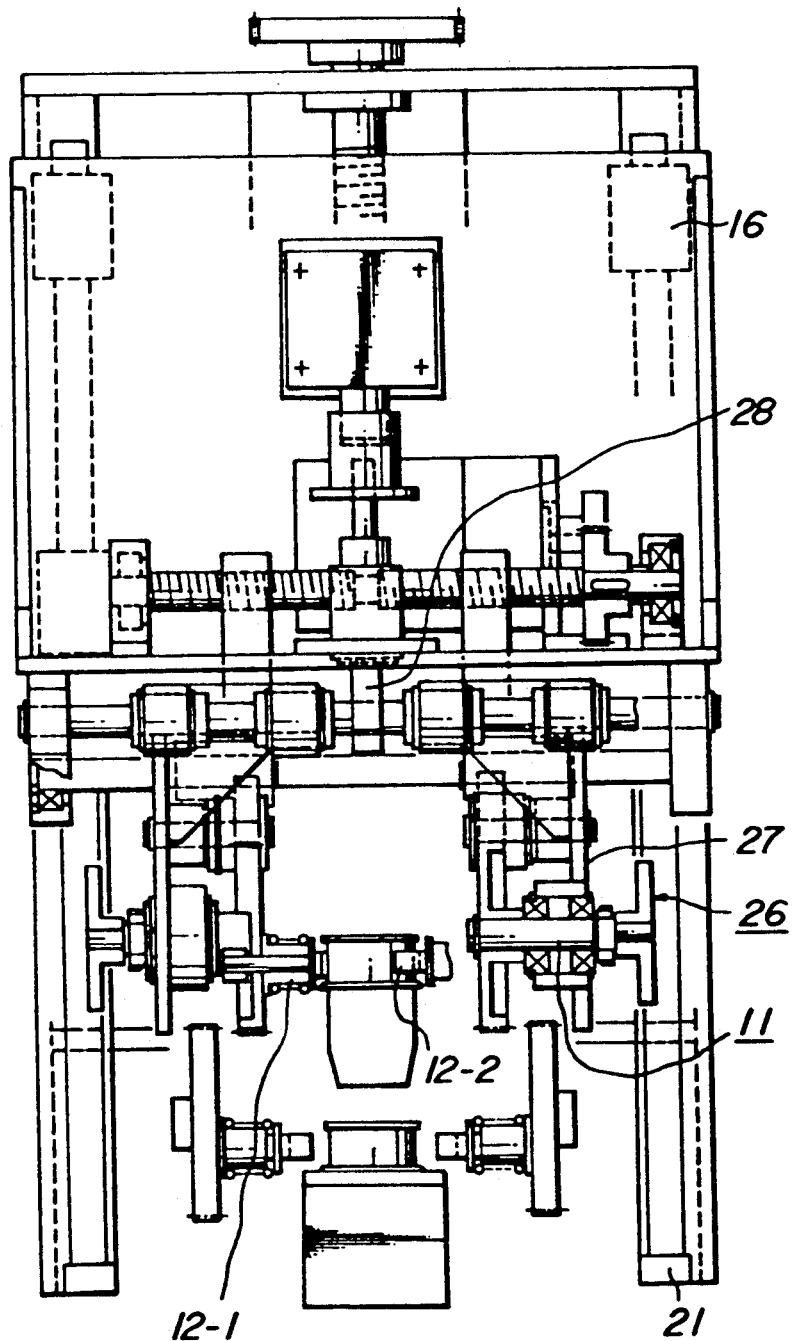
FIG_4

MATERIAL SUPPLY APPARATUS FOR TRANSFERRING POWDERY, GRANULAR AND CONGLOMERATED MATERIALS

This is a division of application Ser. No. 07/235,560 filed Aug. 24, 1988 now U.S. Pat. No. 4,919,342.

CROSS REFERENCE TO RELATED APPLICATION

U.S. patent application Ser. No. 07/414,479, filed Sep. 29, 1989, now U.S. Pat. No. 4,993,646, is also a divisional application of Ser. No. 07/235,560 now U.S. Pat. No. 4,919,342.

BACKGROUND OF THE INVENTION

This invention relates to an apparatus for treating powdery, granular and conglomerate materials and an analyzing method using the apparatus.

In analyzing components of various materials by a method such as the X-ray fluorescence analysis, it is necessary to pretreat the material to be analyzed.

The following four methods have been known as methods for making samples of inorganic materials.
1) A crushing method in which a material is pulverized in order to bring the material into an appropriate condition for the analysis.
2) A vitrifying method in which a material is added with one or a mixture of an alkali metal borate (for example, $Li_2B_4O_7$, $Li_2O.B_2O_3$ and $Na_2B_4O_7$) and heated to be vitrified.
3) An alkali metal carbonate decomposing method in which a material is decomposed by an alkali metal carbonate.
4) A decomposition solution method in which a material in a pressurized vessel is decomposed by a strong acid such as hydrofluoric acid to make it a solution.

The crushing method, among the above methods, is disadvantageous because if the material is at least partially crystalline, the crushed material still includes a crystal structure so that analyzed results with high accuracy could not be obtained in the X-ray fluorescence analysis due to the so-called "mineral effect". Moreover, it takes a long time to crush inorganic materials including non-oxides as components such as silicon nitride, sialon, silicon carbide and the like owing to high hardness. Moreover, there is a risk that the materials may be contaminated by a material of a vessel used for crushing. Therefore, the crushing method has been scarcely used other than in cases not requiring a high accuracy of analysis.

The alkali metal carbonate decomposing method is applicable as a pretreatment method for wet analyses, even for non-oxides. However, this method could not be used for pretreating materials for the X-ray fluorescence analysis due to the fact that decomposed and melted products are high in moisture absorption and are difficult to be removed from used vessels such as platinum dishes and the like.

The vitrifying method, using the alkali metal borate, is disadvantageous because analyzing accuracy is often lowered since vitrification only partially progresses in the case of inorganic materials including non-oxides as components.

Moreover, the decomposition solution method using a strong acid requires a long time (such as 24 hours) for the decompositions. Samples obtained for the analysis are liquid which is preferable for the chemical analysis. However, it is difficult to use such liquid samples in the X-ray fluorescence analysis because of a limitation of an apparatus itself for the X-ray fluorescence analysis.

The so-called "mineral effect", which means that the grain sizes of samples detrimentally affect the accuracy of analysis of the samples, has been known. In order to avoid the mineral effect to carry out the analysis with high accuracy, it is necessary to pulverize samples in powdery, granular and conglomerate states into fine powders of the order of less than 1 $\mu$m and to form formed bodies suitable for analysis. It is preferred that the formed bodies have smooth surfaces for high accuracy analysis. Moreover, it is desired that the formed bodies are rigid and stable for a long period of time in order to facilitate the operation and automation for the analysis. The crushing to forming processes are referred to herein as "pretreatment of samples for the X-ray fluorescence analysis".

The pretreating methods for the X-ray fluorescence analysis have been known as non-addition dry crushing and non-addition wet crushing methods which are carried out in dried and wet conditions without any additions, powdery graphite added dry crushing which is carried out in a dried condition with added graphite (magazine of Japanese Metallurgy Society, vol. 36, page 648, 1972), and binder added wet crushing which is carried out in a wet condition with binders such as styrene-maleic acid copolymer or stearic acid. The powdery graphite has a lubricating effect so that it is effective as a crushing aid for promoting pulverization of samples. On the other hand, binders are effective as a forming or molding aid which gives strength to formed bodies and makes smooth surfaces of the formed bodies. Graphite is also somewhat effective as a molding aid. However, the effect of graphite as the molding aid is insufficient for disk-like formed bodies having diameters of more than 10 mm which are usually used for the X-ray fluorescence analysis.

Although the above non-addition dry crushing method is simple in operation, it is disadvantageous since crushing is sometimes insufficient, analyzing accuracy is lowered due to the mineral effect, and forming samples into disk-like bodies is difficult. The non-addition wet crushing method is disadvantageous since analyzing accuracy is lowered, forming samples into disk-like bodies is difficult and, moreover, since volatilization of solvents is needed. The powdery graphite added dry crushing method is disadvantageous since forming samples into disk-like bodies is difficult, although there is no problem of lowering the analyzing accuracy due to the mineral effect. The binder added wet crushing method is disadvantageous since there is a problem of lowering the analyzing accuracy due to the mineral effect and volatilization of solvents is needed. Therefore, a pretreatment method of samples for X-ray fluorescence analysis has not been proposed, capable of obtaining formed bodies which will bring high accuracy analysis and are rigid and smooth.

In order to supply powdery, granular or conglomerate materials to predetermined positions such as crushers, weighed materials have been manually supplied from hoppers at the predetermined positions to apparatuses such as crushers.

Manual supplying requires skillful operators and obstructs automation of the entire installation line. An automated apparatus, for example, Model HSM-F36 of the HERZOG Company, has been known which comprises, in the proximity of materially supplied positions, a turn table having material vessels provided along a circumference of the turn table, and introducing means for intermittently rotating the turn table.

In such an apparatus, however, the material is supplied into the hoppers with the aid of centrifugal forces caused by rotation of the material vessels driven by the introducing means. Therefore, all the materials could not be supplied into the hoppers exactly. Moreover, the turn table is disadvantageous since material is introduced into the hoppers only in a predetermined order due to the fact that the turn table performs its intermittent rotation only in connection with the material vessels.

Various crushers for crushing samples have been known. With these crushers, a crushing operation is carried out with crushing vessels made of, for example, tungsten carbide (WC) regardless of whether the operation is manual or automatic.

In this case, introduction of samples and removal of crushed samples are effected by transferring crushing vessels from the crushers to working tables. Every time kinds of samples are changed, the crushing vessels mush also be transferred from the crushers to the cleaning means for cleaning the vessels. These troublesome transferring of the vessels have been manually carried out.

The vessels made of tungsten carbide or chromium steel are so heavy that the manual operation for transferring the vessels is disadvantageous to safety and efficiency. On the other hand, when organic binders are added to samples to be crushed, the binders are likely to stick to inner walls of the crushing vessels. Therefore, the attached crushed samples could not be completely removed from the crushing vessels without manual cleaning.

In various analyzing apparatuses, particularly the fluorescent X-ray analyzing apparatus, these apparatuses have been supplied with samples to be analyzed as formed bodies in predetermined shapes or accommodated in predetermined exclusive holders. In order to make such formed bodies of samples or insert samples into the holders, separate pressing apparatuses or holder loading and unloading apparatuses are needed.

In this case, the precise X-ray fluorescence analysis for various kinds of samples is accomplished by manually operating the formation of the samples and transference of the samples to the apparatuses. However it is impossible to automatically supply the samples to fluorescence X-ray analyzing apparatuses to form automatic analyzing systems. Moreover, when existing holder loading and unloading apparatuses are used, only one or two reference samples are held at a time. Therefore, such existing apparatuses could not be used for automatically analyzing various kinds of samples continuously and precise X-ray fluorescence analysis could not be realized, so that the use of the existing apparatuses is limited to particular analyses. Such a limitation of use results also from the fact that the holders are prohibitively expensive and particular. Thus, they could not be provided in large quantities.

In order to determine predetermined compositions in samples, the X-ray fluorescence analysis with X-ray has been used and various fluorescent X-ray analyzing apparatuses have been known. With such fluorescent X-ray analyzing apparatuses, in supplying a sample to the apparatus the sample must be formed in a predetermined shape and set at a predetermined position in a sample holder. Moreover, the sample must be pretreated in order to avoid the influence of physical and chemical factors of the sample on fluorescence X-ray intensity and to improve the analyzing accuracy.

For this purpose, in the case of inorganic samples such as ceramics or the like, it is required to use a crusher for crushing an inorganic raw material into predetermined grain sizes and a press for forming the crushed material into predetermined shapes. Thus, produced samples are set in the sample holder for the X-ray fluorescence analysis.

With hitherto used apparatuses, introducing the samples into the apparatuses is not reliably effected. Transferring the samples between the apparatuses and setting the samples into the apparatuses must be effected by skillful operators. Further, even with new systems partially automated with such operations, it might be ineffective, if not impossible, to carry out various kinds of samples.

SUMMARY OF THE INVENTION

It is a primary object of the invention to provide an apparatus for treating powdery, granular and conglomerate materials and an analyzing method using the apparatus, which eliminate all the disadvantages of the prior art.

It is a further object of the invention to provide an improved material supply apparatus which eliminates all the disadvantages of the prior art and is capable of selectively introducing any materials and introducing materials automatically and exactly.

In order to achieve this object, a material supply apparatus according to the invention comprises: material vessels for receiving therein materials under any powdery, granular or conglomerate condition, material racks for accommodating therein a plurality of the material vessels, a material vessel pooling unit for holding the material racks to be driven, a material vessel transferring unit for selecting a predetermined material vessel and taking it out from said material racks and transferring it to a predetermined position, and control means for controlling operations of the material vessel pooling unit and the material vessel transferring unit.

With this arrangement, the supply of samples is carried out by controlling via control means operations of the material vessel pooling unit for driving the material rack accommodating therein sample vessels and the material vessel transferring unit for selectively transferring the material vessel, so that any materials can be automatically supplied in a predetermined order by inputting the predetermined order into the control means.

In the case that the material vessel transferring unit comprises: the grasping means, the lifter, the transfer means and the turn-over introducing means, after positioning the material vessel into a predetermined position by the grasping means, the lifter and the transfer means, the material in the vessel is completely supplied by the turn-over introducing means, thereby supplying the material more exactly.

BRIEF DESCRIPTION OF THE DRAWINGS

FIG. 1 is a plan view illustrating one example of a material supply apparatus according to the invention together with an automatic crusher;

FIG. 2 is a front elevation illustrating the material supply apparatus and the automatic crusher shown in FIG. 1;

FIG. 3 is a front elevation of a material vessel transferring unit in the material supply apparatus shown in FIG. 1;

FIG. 4 is a side view of the material vessel transferring unit.

DESCRIPTION OF THE PREFERRED EMBODIMENTS

FIGS. 1 and 2 illustrate in plan and front views one example of the material supply apparatus according to the invention.

In this embodiment, above an automatic crusher 1 and on a base 5 a material supply unit 4 is provided comprising a material vessel pooling unit 2 and a material vessel transferring unit 3 so that particular materials are selected from various kinds of materials and introduced into the automatic crusher 1. Material racks 6-1 to 6-8 of the material vessel pooling unit 2 receive ten material vessels 7, respectively. There are totally (8×10) material vessels 7. Before starting the operation, positions and kinds of the eighty materials are inputted into a control means 8, on the basis of which inputted data the materials are supplied. The material vessel pooling unit 2 is able to move in both directions shown by an arrow so that a rack or rack 6-1 in this embodiment positioned at a rack moving position, a, is transferred to a material introducing position shown in the drawing. The materials in the material vessels 7 at the material introducing position are held and transferred by the material supply unit 4 in a predetermined order so as to be supplied into a material introducing opening of the automatic crusher 1.

FIGS. 3 and 4 illustrate in front and side views one example of the material vessel transferring unit 3 of the material supply unit. In the embodiment shown in FIGS. 3 and 4, the material vessel transferring unit 3 comprises grasping means 11, a lifter 16, transfer means 21 and turn-over introducing means 26. The grasping means 11 embraces and holds the material vessel 7 by supports 12-1 and 12-2 on both sides. The lifter 16 raises and lowers the material vessel 7, embraced by the grasping means 11. The lifter 16 is raised or lowered by a motor 18 which drives ball screws 17 to raise or lower nuts 19 engaged with the ball screws 17. The transfer means 21 translately moves, relative to the base 5, along guides provided on the base 5. The turn-over introducing means 26 comprises a turn-over mechanism 27 for turning over the embraced material vessel by 180°, and an introducing mechanism 28 for striking a bottom of the material vessel 7 once or twice to remove the congregated material at the inside of the bottom from the vessel.

The material vessel transferring unit 3 described above is moved by the transfer means 21 to a position of the predetermined material vessel 7 in the material rack 6-1 at the material introducing position. Then the material vessel transferring unit 3 is lowered to the position of the material vessel 7 where the vessel 7 is embraced by the grasping means 11. The material vessel transferring unit 3 is then once raised embracing the vessel 7 by the lifter 16. Thereafter, the transferring unit 3 is transferred by the transfer means 21 to the material introducing port of the automatic crusher 1. From this position, the unit 3 is lowered by the lifter 16 to the proximity of the material introducing port, and thereafter the unit 3 is turned over through 180° by the turn-over mechanism 27 of the turn-over introducing means 26. Finally, the introducing mechanism 28 strikes once or twice the bottom of the material vessel 7 to supply the remaining congregated material at the inside of the bottom into the material introducing port. The material supplying operation is completed in this manner. Moreover, all the operations above described are effected by control of the control means 8.

As can be seen from the above explanation, the material supply apparatus supplies material by controlling the operations of the material vessel pooling unit and the material vessel transferring unit by the control means. Therefore, a predetermined order of the operations is previously inputted in the control means so that desired materials can be selectively introduced into a required apparatus. Moreover, the introduction of the material can be effected automatically and exactly.

It is further understood by those skilled in the art that the foregoing description is that of preferred embodiments of the disclosed invention and that various changes and modifications may be made in the invention without departing from the spirit and scope thereof.

What is claimed is:

1. A material supply apparatus comprising:
    a base member;
    a material vessel pooling unit arranged on said base member and being movable reciprocally in a direction perpendicular to a longitudinal direction of said base member;
    a plurality of elongate material racks arranged side by side in said material vessel pooling unit such that each of said elongate material racks is arranged in the longitudinal direction of said base member;
    a plurality of material vessels arranged in each of said elongate material racks to form a single-layered array of material vessels accommodated in said material vessel pooling unit;
    a material vessel transferring unit arranged on said base member and being movable reciprocally in the longitudinal direction of said base member in a first direction to a first position where said material transferring unit removes a selected material vessel from a selected elongate material rack, and in a second direction diametrically opposed to said first direction to a second position where said material vessel transferring unit disposes of a material contained in said selected material vessel; and
    control means for controlling the reciprocal movement of said material vessel pooling unit to align said selected elongate material rack with a third position longitudinally corresponding to said first position, and for controlling the reciprocal movement of said material vessel transferring unit between said first position and said second position.

2. The material supply apparatus of claim 1, wherein said material vessel transferring unit comprises grasping means for grasping said selected material vessel from said selected elongate material rack.

3. The material supply apparatus of claim 1, wherein said material vessel transferring unit comprises:
    grasping means for grasping said selected material vessel from said selected elongate material rack;
    lifting means for raising said grasping means during movement of said material vessel transferring unit and for lowering said grasping means to engage and grasp said selected material vessel;
    transfer means for reciprocally moving said material vessel transferring unit between said first position and said second position; and rotatable disposal means for rotating the grasped, selected material vessel from upright position to an inverted position to dispose of material contained in said selected material vessel when said material vessel transferring unit is arranged in said second position.

4. The material supply apparatus of claim 3, wherein said rotatable disposal means further comprises means for intermittently striking the bottom of said inverted selected material vessel to assist in complete removal of the material contained therein.

* * * * *